(12) United States Patent
Shvetsov et al.

(10) Patent No.: US 10,405,917 B2
(45) Date of Patent: Sep. 10, 2019

(54) ELECTROSURGICAL DEVICE WITH VACUUM PORT

(71) Applicant: Buffalo Filter LLC, Lancaster, NY (US)

(72) Inventors: Kyrylo Shvetsov, Depew, NY (US); Michael J. Miller, Depew, NY (US); Gregory Pepe, Lancaster, NY (US); Samantha Bonano, Williamsville, NY (US)

(73) Assignee: BUFFALO FILTER, LLC, Lancaster, NY (US)

( * ) Notice: Subject to any disclaimer, the term of this patent is extended or adjusted under 35 U.S.C. 154(b) by 459 days.

(21) Appl. No.: 15/045,482

(22) Filed: Feb. 17, 2016

(65) Prior Publication Data

US 2016/0157918 A1 Jun. 9, 2016

Related U.S. Application Data

(63) Continuation-in-part of application No. 13/021,494, filed on Feb. 4, 2011, now Pat. No. 9,289,261, and a
(Continued)

(51) Int. Cl.
| | |
|---|---|
| *A61B 18/14* | (2006.01) |
| *A61B 18/00* | (2006.01) |
| *A61B 90/30* | (2016.01) |

(52) U.S. Cl.
CPC .......... *A61B 18/1477* (2013.01); *A61B 90/30* (2016.02); *A61B 2018/00196* (2013.01);
(Continued)

(58) Field of Classification Search
CPC . A61B 18/1477; A61B 18/14; A61B 18/1402; A61B 18/148; A61B 18/1485;
(Continued)

(56) References Cited

U.S. PATENT DOCUMENTS

| | | |
|---|---|---|
| 3,825,004 A | 7/1974 | Durden, III |
| 5,192,267 A | 3/1993 | Shapira et al. |

(Continued)

FOREIGN PATENT DOCUMENTS

GB 2406793 A 4/2005

*Primary Examiner* — Michael F Peffley
(74) *Attorney, Agent, or Firm* — William R. Zimmerli (57) ABSTRACT

An electrosurgical device having an electrode with a first portion whose exterior is electrically uninsulated, a second portion whose exterior is electrically insulated, and a third portion. An elongated hollow body has an internal cavity, a front end, a rear end, an external surface. An electrical circuit is arranged within the body. The second portion of the electrode is not surrounded by the hollow body. A first button is arranged on the external surface of the body for controlling a current flow at a first level. A vacuum tube is slidably engaged by the body. The vacuum tube is configured with a blade holder to reversibly receive the third portion of the electrode such that electrical contact is made between the electrode and a conductor which is connected to the electrical circuit by electrical connector. A vacuum outlet port is arranged near the rear end, and the outlet port, internal cavity, and vacuum inlet are in fluid communication with each other.

16 Claims, 12 Drawing Sheets

Related U.S. Application Data continuation-in-part of application No. 13/840,693, filed on Mar. 15, 2013.

(60) Provisional application No. 61/301,328, filed on Feb. 4, 2010, provisional application No. 61/318,023, filed on Mar. 26, 2010, provisional application No. 61/645,051, filed on May 9, 2012.

(52) U.S. Cl.
CPC ............... *A61B 2018/00595* (2013.01); *A61B 2018/00601* (2013.01); *A61B 2018/00607* (2013.01); *A61B 2018/00922* (2013.01); *A61B 2018/00958* (2013.01); *A61B 2018/1412* (2013.01); *A61B 2018/1475* (2013.01); *A61B 2218/008* (2013.01)

(58) Field of Classification Search
CPC ........... A61B 2018/00589; A61B 2018/00577; A61B 2018/0091; A61B 2018/00607; A61B 2018/00327; A61B 2018/00916; A61B 2018/00964; A61B 2018/1412; A61B 2018/00196; A61B 2018/00958; A61B 2018/1475

See application file for complete search history.

(56) References Cited

U.S. PATENT DOCUMENTS

| | | | |
|---|---|---|---|
| 5,234,428 A | | 8/1993 | Kaufman |
| 5,269,781 A * | | 12/1993 | Hewell, III ........ A61B 18/1402 604/35 |
| 5,318,565 A * | | 6/1994 | Kuriloff ............. A61B 18/1402 604/119 |
| 5,413,575 A | | 5/1995 | Haenggi |
| 5,626,568 A | | 5/1997 | Yeh |
| 5,709,675 A * | | 1/1998 | Williams ............... A61B 18/00 604/22 |
| 5,730,742 A | | 3/1998 | Wojciechowicz |
| 6,146,353 A * | | 11/2000 | Platt, Jr. ................. A61B 18/00 604/22 |
| 6,635,034 B1 | | 10/2003 | Cosmescu |
| 6,733,495 B1 * | | 5/2004 | Bek ........................ A61B 18/00 606/34 |
| 2001/0018586 A1 | | 8/2001 | Cosmescu |
| 2002/0019596 A1 | | 2/2002 | Eggers |
| 2004/0162553 A1* | | 8/2004 | Peng .................. A61B 18/1402 606/42 |
| 2005/0060974 A1 | | 3/2005 | Palmerton |
| 2006/0264928 A1* | | 11/2006 | Kornerup ........... A61B 18/1402 606/45 |
| 2009/0018539 A1 | | 1/2009 | Comescu |
| 2009/0054890 A1* | | 2/2009 | DeCarlo ............ A61B 18/1402 606/34 |
| 2009/0062791 A1* | | 3/2009 | Lee .................... A61B 18/1402 606/45 |
| 2010/0130972 A1 | | 5/2010 | Yambor |
| 2010/0145333 A1* | | 6/2010 | Dethier .............. A61B 18/1402 606/42 |
| 2011/0190768 A1 | | 8/2011 | Shvetsov |
| 2012/0067212 A1 | | 3/2012 | Warren |
| 2012/0286179 A1 | | 11/2012 | Palmerton |
| 2014/0303449 A1 | | 10/2014 | Balog |

\* cited by examiner

ELECTROSURGICAL DEVICE WITH VACUUM PORT

CROSS-REFERENCE TO RELATED APPLICATION

The present application claims the benefit of U.S. patent application Ser. No. 13/021,494 filed on Feb. 4, 2011, which issued as U.S. Pat. No. 9,289,261 on Mar. 22, 2016, and entitled "Electrosurgical Device with Vacuum Port" which claims the benefit of U.S. Provisional Patent Application No. 61/301,328 filed on Feb. 4, 2010 and U.S. Provisional Patent Application No. 61/318,023, filed on Mar. 26, 2010, all of which are incorporated herein by reference. The present application also claims the benefit of U.S. patent application Ser. No. 13/840,693 filed on Mar. 15, 2013, and entitled "Electrosurgical Device with Vacuum Port" which claims the benefit of U.S. Provisional Patent Application No. 61/645,051, filed on May 9, 2012, which are incorporated herein by reference.

FIELD OF THE INVENTION

The present invention relates generally to smoke evacuation, and, more specifically, to an electrosurgical device with smoke evacuation during medical procedures.

BACKGROUND

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons.

BRIEF SUMMARY OF THE INVENTION

With parenthetical reference to the corresponding parts, portions or surfaces of the disclosed embodiment, merely for the purposes of illustration and not by way of limitation, the present invention provides an electrosurgical device comprising: an electrode (26) having a first portion (27) whose exterior is electrically uninsulated, a second portion (28) whose exterior is electrically insulated, and a third portion (30); an elongated hollow body (23) having an internal cavity, a front end, a rear end, an external surface (44), and an electrical circuit arranged within the body, and where the second portion of the electrode is not surrounded by the hollow body. A first button (41) is arranged on the body's external surface (44) for controlling a current flow at a first level. A vacuum tube (29) is slidably engaged by the body and has an inlet (38) generally facing the front end of the body (23). The vacuum tube (29) is arranged to surround the electrode (26). The vacuum tube (29) is also configured to reversibly receive the third portion (30) of the electrode (26) in a separate channel (33) formed at the bottom of the tube (29) such that electrical contact is made between the electrode (26) and a conductor (56). The conductor (56) is connected to the electrical circuit by an electrical connector (59). A vacuum outlet port (24) is arranged near the rear end, and the outlet port, internal cavity, and vacuum inlet are in fluid communication with each other.

The body may be ergonometrically shaped to be received by a user's hand. The inlet to the vacuum tube (29) may be shaped to have a cross section parallel to a user's line of sight towards said electrode (26) when using said device (20). The body (23) may be pencil shaped and may contain friction striations (21). The friction striations may be curved. The electrode (26) may be monopolar, bipolar, or sesquipolar.

The device may have a second button (47) for controlling a current flow at a second level to the electrode (26), and may have a third button to control the vacuum source.

The device may also have: a light source arranged to illuminate an area near the electrode, a battery for providing power to the light source, a button for controlling the illumination light, a swivel joint between the body and the outlet port, and an electrical line may pass through the swivel joint to the electrical circuit.

A filter may be arranged within the internal cavity and the filter may have an RFID tag containing filter information. The vacuum tube inlet may have a substantially rectangular cross section.

In another form, an electrosurgical device (120) comprises: an electrode (126); an elongated hollow body (123) having an internal cavity, a front end, a rear end, an external surface (144), and an electrical circuit arranged within the body (123). The hollow body (123) is shaped to have an ergonometric orientation complementary to a user's hand. A first button (141) controls a current flow at a first level to the electrode (126) and is arranged on the external surface (144). A vacuum tube (129) is slidably engaged by the body (123) and has an inlet shaped to have a cross section parallel to a user's line of sight towards said electrode (126) when using said device (120). The vacuum tube (129) surrounds the electrode (126). The vacuum tube (129) has a blade holder/channel (133) configured to reversibly receive the third portion (130) of the electrode (126) in the center of the vacuum tube (129). A vacuum outlet port is arranged near the rear end of the body (123) and the outlet port, internal cavity, and vacuum inlet are in fluid communication with each other.

The device (120) may be configured to have an electrically insulated portion not surrounded by the body (123) when the electrode (126) is received by the body (123). The body (123) may be pencil shaped and may contain friction striations and the striations may be curved. The electrode (126) may be monopolar, bipolar, or sesquipolar.

The device (120) may have a second button (147) for controlling a current flow at a second level to said electrode (126) or a third button for controlling a vacuum source. The inlet may have a substantially rectangular cross section. The device may also have a light source arranged to illuminate an area near the electrode; a battery for providing power to the light source; a button for controlling the illumination light; and a swivel joint between the body and the outlet port. An electrical line may pass through said swivel joint to the electrical circuit.

The device may contain a filter arranged within the internal cavity and may contain an RFID tag containing filter information.

In another form, an electrosurgical device (220) is provided comprising: an electrode (226); an elongated hollow body (223) having an internal cavity, a front end, a rear end, an external surface, and an electrical circuit arranged within the body (223). The hollow body (223) is shaped to have an ergonometric orientation complementary to a user's hand. A first button (241) controls a current flow at a first level to the electrode (226) and is arranged on the external surface. A vacuum tube (229) is engaged by the body (223) and has an inlet shaped to have a cross section parallel to a user's line of sight towards said electrode (226) when using said device (220). The vacuum tube (229) is configured to reversibly receive the third portion (230) of the electrode (226) in a blade holder/channel (233) mounted in the bottom of the vacuum tube (229). The vacuum tube (229) surrounds the electrode (226). A vacuum outlet port may be arranged near the rear end, and the outlet port, internal cavity, and vacuum inlet are in fluid communication with each other.

The device has means for preventing the vacuum tube from obstructing a user's view of said electrode and means for removing the electrode without electrically contacting the electrode. The means for preventing the vacuum tube from obstructing a user's view may comprise a slidable engagement between the vacuum tube and the body. The means for preventing the vacuum tube from obstructing a user's view may comprise an inlet shaped to have a cross section perpendicular to a user's line of sight towards the electrode when using the device. The means for removing the electrode without electrically contracting the electrode may comprise an insulation coating on the electrode which remains accessible to a user's hand when the electrode is received by the body.

DESCRIPTION OF THE PREFERRED EMBODIMENTS

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Figure 1:
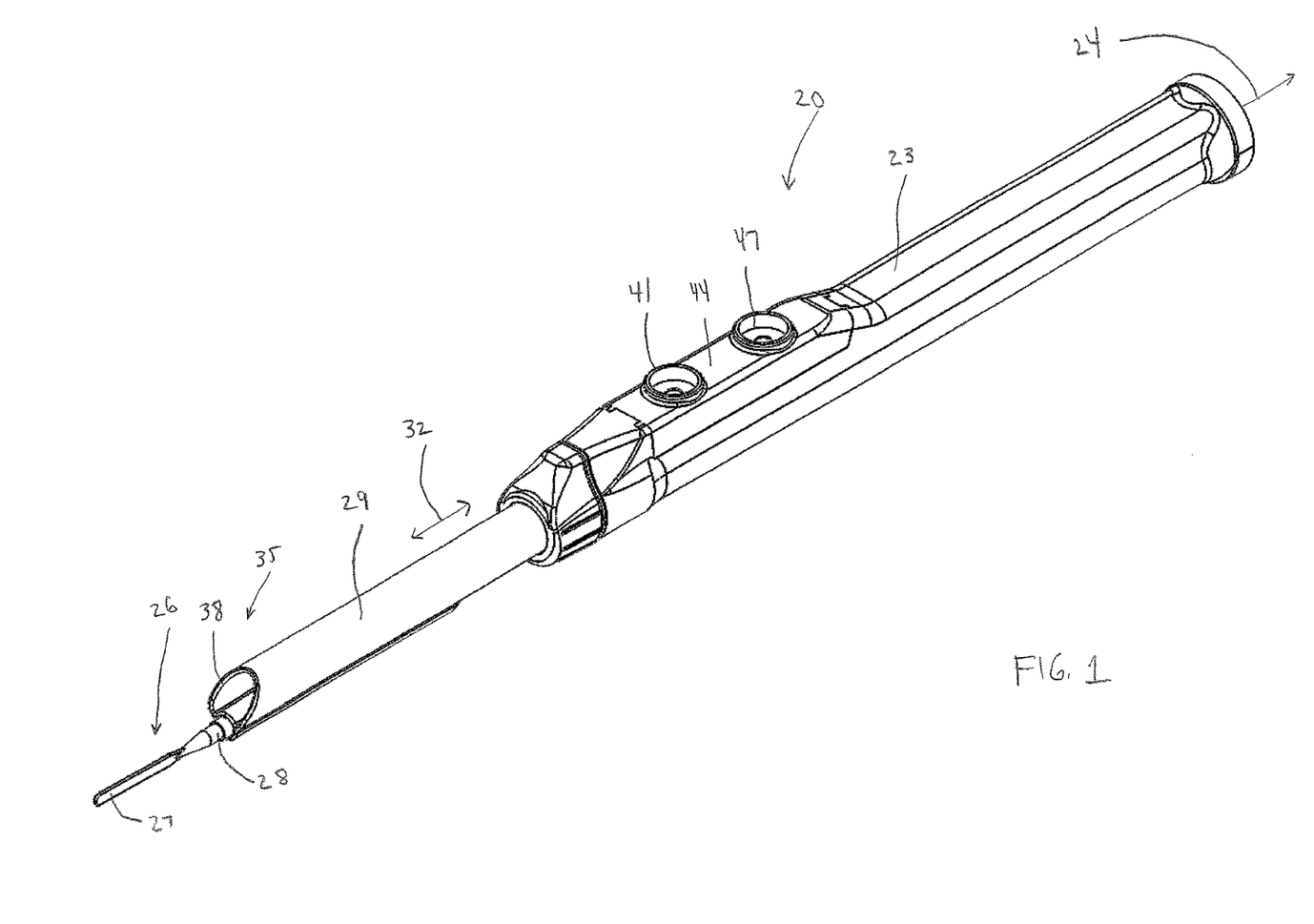
FIG. 1 is a perspective view of a first embodiment of the electrosurgical device of the present invention.

Referring now to the drawings, and more particularly to FIG. 1 thereof, this invention provides an electrosurgical pen 20 having a body 23. The body 23 may be ergonomically shaped to be received by a user's hand. The body 23 may be pencil shaped and may have a longitudinal axis 24. On the left side of the figure, an electrode 26 is removably attached to a vacuum tube 29. The electrode 26 may have a uninsulated end portion 27, insulated portion 28, and a mounting portion 30. The vacuum tube 29 is mounted on the body 23 and may extend telescopically from the body 23 in an axial direction 32. The distal end 35 of the vacuum tube 29 comprises an inlet 38 shaped to have a cross section parallel to a user's line of sight towards said electrode 26 when using the pen 20.

The pen 20 may be provided with a first button 41 arranged on the external surface 44 of the body 23. The first button 41 may control the current flow to the device at a first level. The pen 20 may have a second button 47 for controlling a current flow at a second level to the electrode 26. Additional buttons may be added for controlling the vacuum source, a light source or the like.

Figure 2:
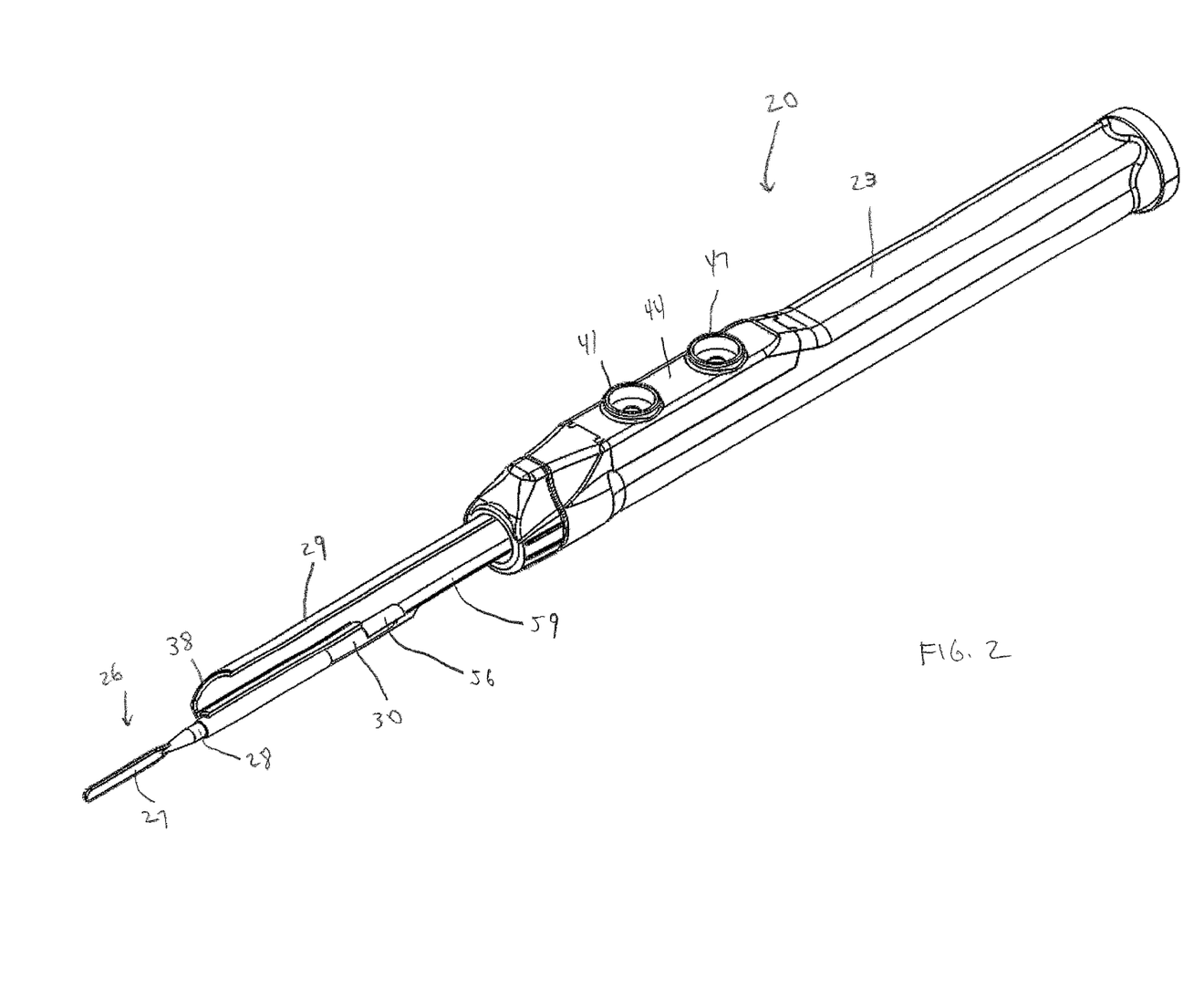
FIG. 2 is a partial cutaway perspective view of the device of FIG. 1.

Turning to FIG. 2, a portion of the vacuum tube 29 has been removed for clarity. The tube 29 has a set of opposed walls 50, 53 (FIG. 4) forming a channel/blade holder 33 at the bottom of the tube 29 for receiving the electrode 26. At the end of the channel/blade holder 33, there is a conductor 56 that is electrically connected by an electrical connector 59 to a circuit (not shown) inside the body 23 that provides current to the electrode 26 for operation of the device 20. The first and second buttons 41, 47 are electrically associated with the electric circuit inside the body 23 to provide different levels of current to flow to the electrode 26 depending on whether the device 20 is being used for cutting or coagulating. The end 27 of the electrode 26 is uninsulated for use as an electric blade for cutting and cauterizing during medical procedures. A midportion 28 of the electrode is insulated so that the user can remove the electrode 26 from the device. A base portion 30 of the electrode 26 is designed to make contact with the conductor 56 at the end of the channel 33 in the tube 29 and to removably attach the electrode 26 to the device 20 inside the tube 29.

Figure 3:
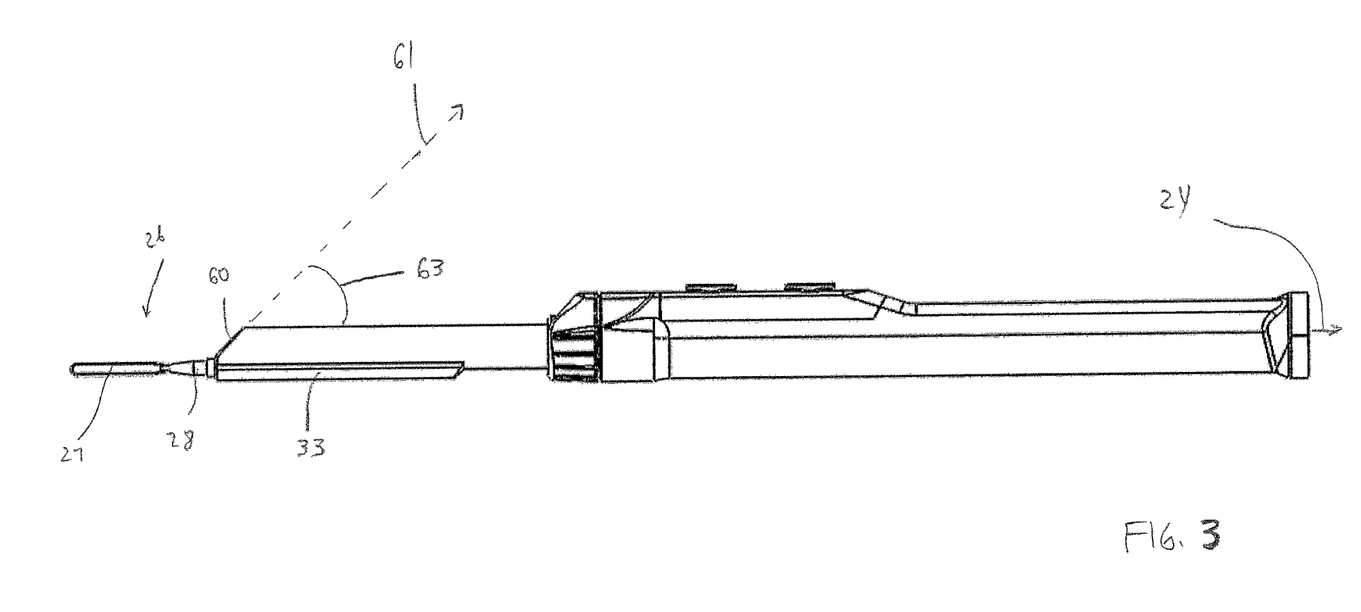
FIG. 3 is a side elevational view of the device of FIG. 1.

In FIG. 3, the placement of the blade holder/channel 33 at the bottom of the tube 29 is shown. The electrode 26 slides into the blade holder 33 and is held in place by a frictional fit inside the channel. As shown the end of the tube 29 is shaped to have a cross section 60 disposed along an axis 61 at an acute angle 63 relative to the longitudinal axis 24 of the device 20 such that the angle of the chamfer at the end of the tube 29 is parallel to a user's line of sight toward the electrode 26 when using the pen 20. The vacuum tube 29 may be telescopically or fixedly attached to the body 23 of the device 20 in the position shown. Electrodes 26 having different lengths, widths, etc. may be switched in and out of the blade holder 33 in the device 20 to accommodate different patients and different procedures.

Figure 4:
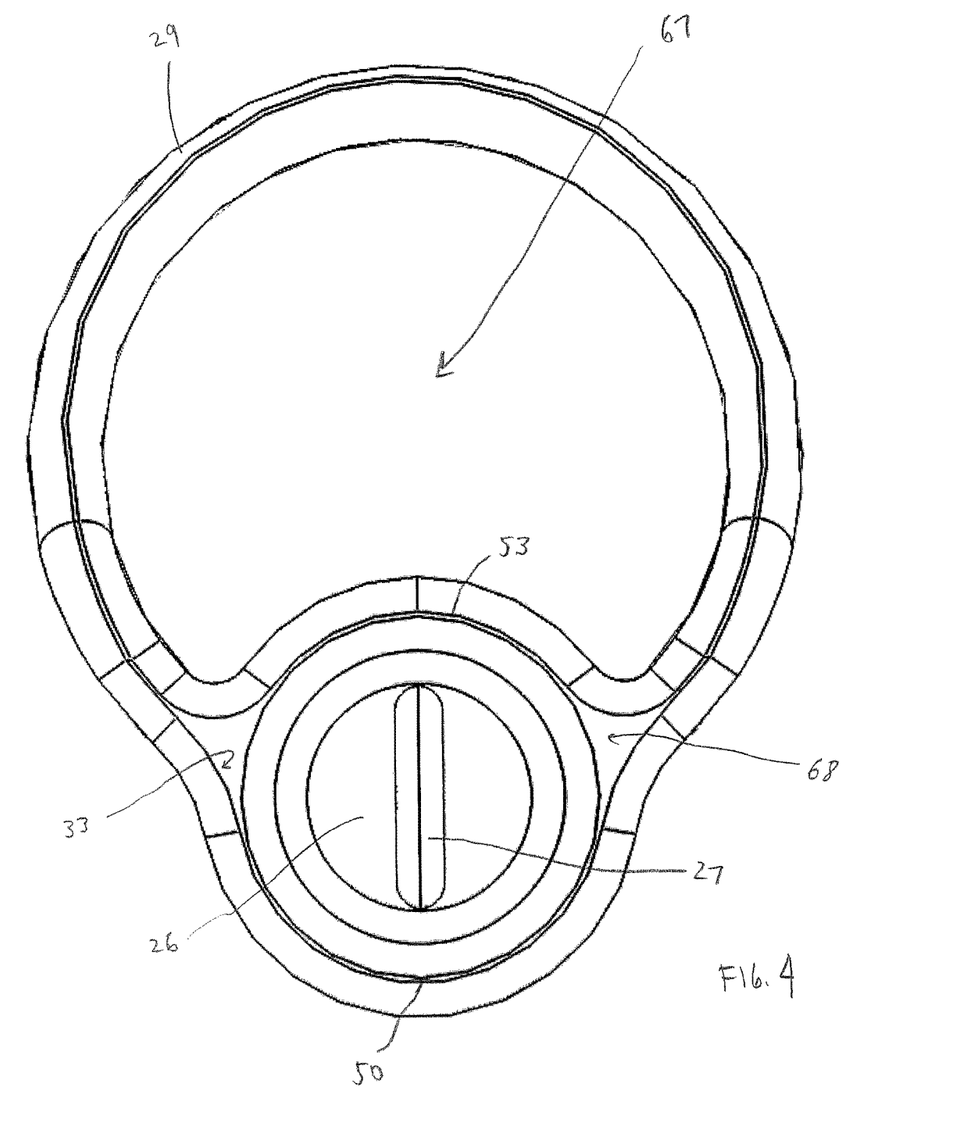
FIG. 4 is a front elevational view of the tube and electrode of the device of FIG. 1.

Turning to FIG. 4, a separate channel 33 may be formed in the tube 29 for receiving the electrode 26. The surgical smoke is evacuated through the passageway 67 formed at the top of the tube 29. An opening 68 provides entry into the channel 33 formed between curved walls 50 and 53 in the bottom portion of the tube 29. The channel 33 is sized to receive the electrode 26. The opening 68 leads to the channel 33 which extends axially along the length of the tube 29. At the end of the channel 33, the base 30 of the electrode 26 contacts the conductor 56 to establish electrical contact between the electrode 26 and the electrical circuit in the device 20. The electrical circuit in the device 20 provides current to the electrode 26. The current may be provided at different levels depending on the application. For cutting, a higher current level is required, whereas, coagulation requires less current.

Figure 5:
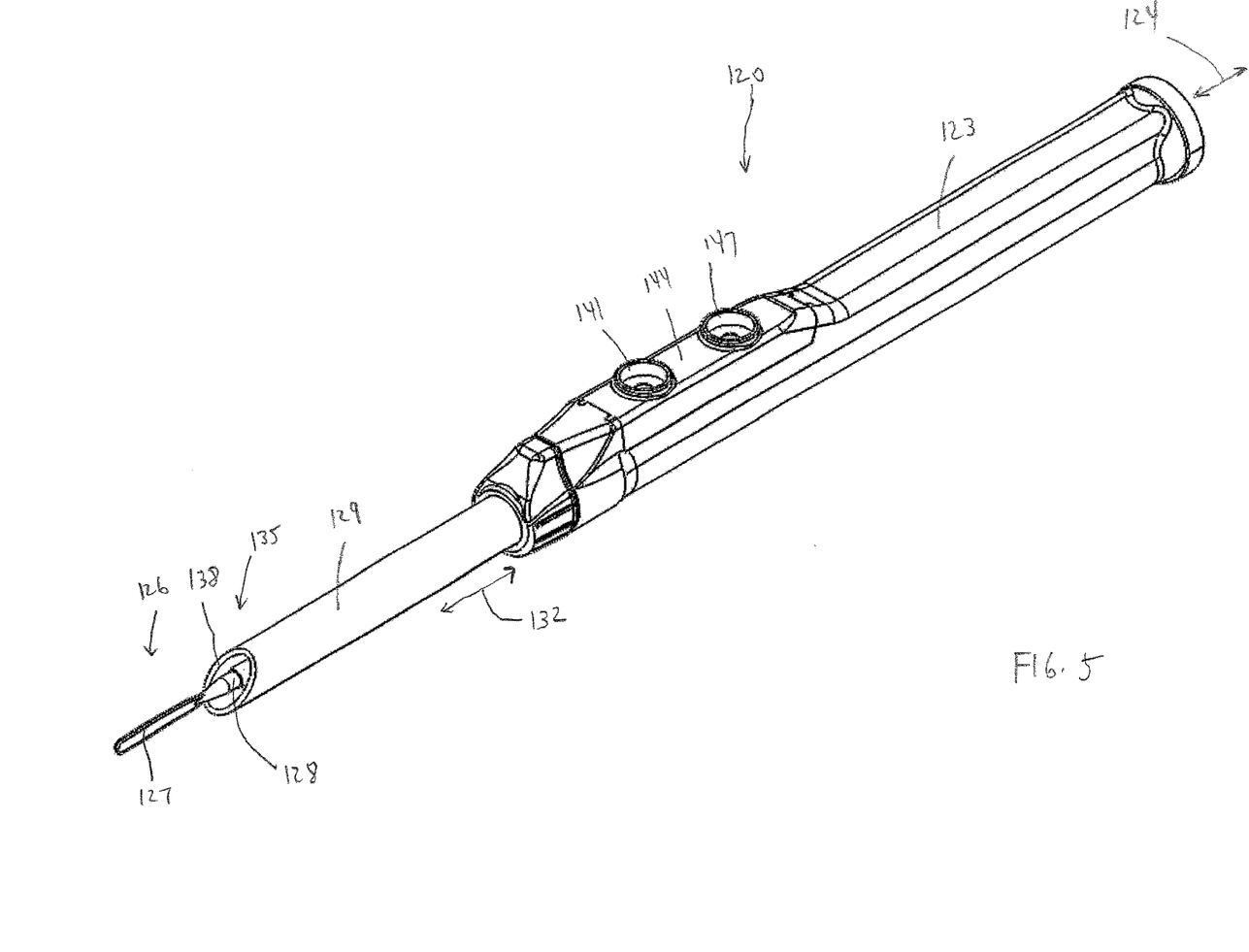
FIG. 5 is a perspective view of an alternate embodiment of the electrosurgical device of the present invention.

In FIG. 5, an alternate embodiment of the electrosurgical device is shown. In contrast to the embodiment of FIGS. 1-4, an electrode 126 is held in the center of a tube 129 by a blade holder 133 (FIG. 6) disposed inside the tube 129. The body 123 may be ergonomically shaped to be received by a user's hand. The body 123 may be pencil shaped and may have a longitudinal axis 124. On the left side of the figure, an electrode 126 is removably attached to a vacuum tube 129. The electrode 126 may have a uninsulated end portion 127, insulated portion 128, and a mounting portion 130. The vacuum tube 129 is telescopically mounted on the body 123 and extends from the body in an axial direction 132. The distal end 135 of the vacuum tube 129 comprises an inlet 138 shaped to have a cross section parallel to a user's line of sight toward the electrode 126 when using the pen 120.

The pen 120 may be provided with a first button 141 arranged on an external surface 144 of the body 123. The first button 141 may control the current flow to the device 120 at a first level. The pen 120 may have a second button 147 for controlling a current flow at a second level to the electrode 126. Additional buttons may be added for controlling the vacuum source, a light source or the like.

Figure 6:
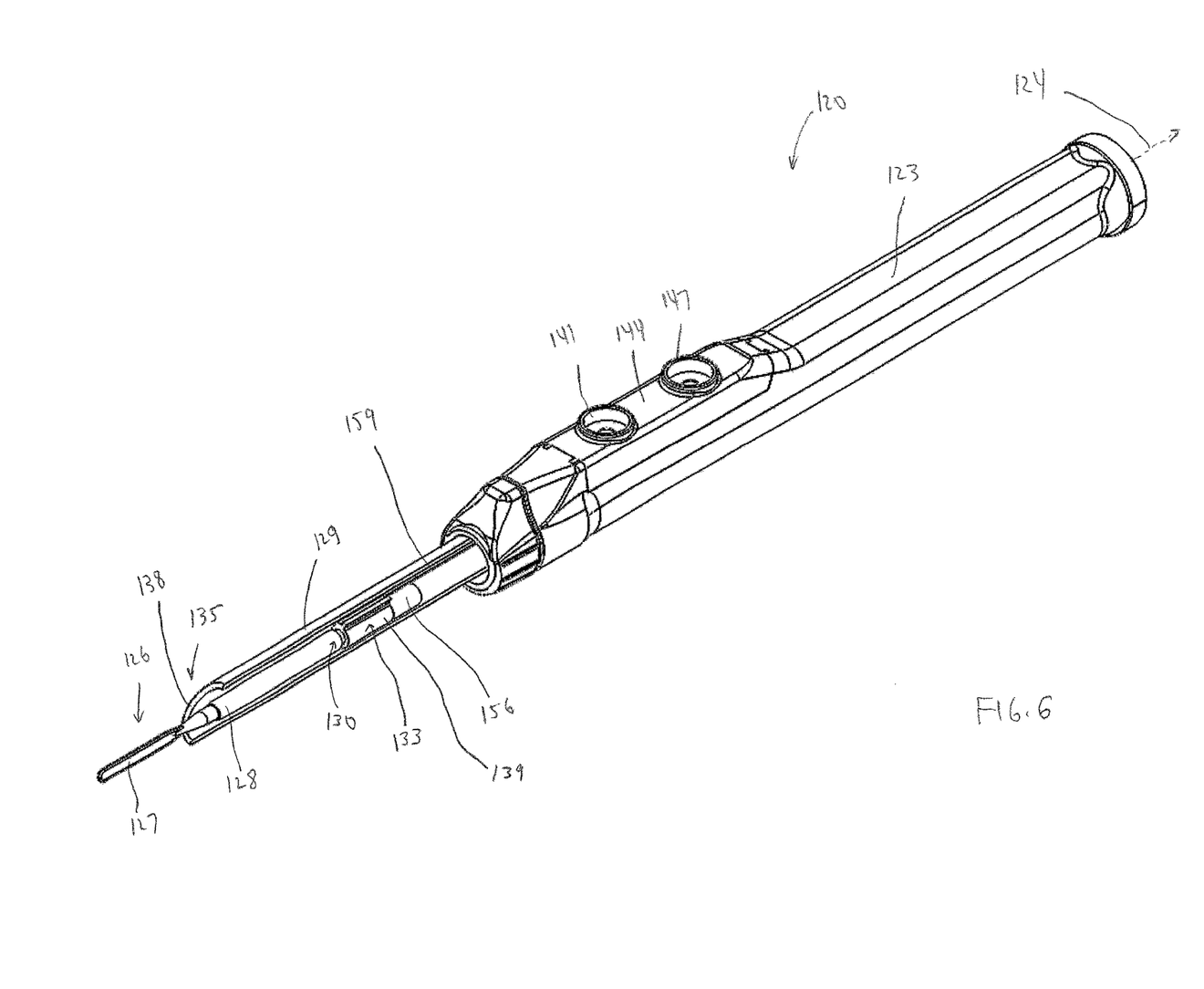
FIG. 6 is a partial cutaway perspective view of the electrosurgical device of FIG. 5.

Turning to FIG. 6, a portion of the vacuum tube 129 has been removed for clarity. The tube 129 has a channel/blade holder 133 defined therein for receiving the electrode. At the end of the channel 133, there is a conductor 156 that is electrically connected by an electrical connector 159 to a circuit inside the body 123 that provides current to the electrode 126 for operation of the device 120. The first and second buttons 141 and 147 are electrically associated with the electric circuit inside the body 123 to provide different levels of current to flow to the electrode 126 depending on whether the device 120 is being used for cutting or coagulating. The end 127 of the electrode 126 is uninsulated for use as an electric blade for cutting and cauterizing during medical procedures. A midportion 128 of the electrode 126 is insulated so that the user can remove the electrode 126 from the device 120. A base portion 130 of the electrode 126 is designed to make contact with the conductor 156 at the end of the channel 133 in the tube 129 and to removably attach to the device 120 inside the tube 129. The blade holder 133 is mounted inside the vacuum tube 129. The blade holder 133 has a longitudinal channel formed therein for receiving the electrode 126. The body 139 of the blade holder 133 is round and fits inside the center of the vacuum tube 129. The blade holder 133 has a pair of ribs 180, 183 (FIG. 8) extending from one side that engage with the inside of the tube 129. The blade holder 133 provides for the flow of surgical smoke around the blade holder 133 and the ribs 180, 183 through the tube 129.

Figure 7:
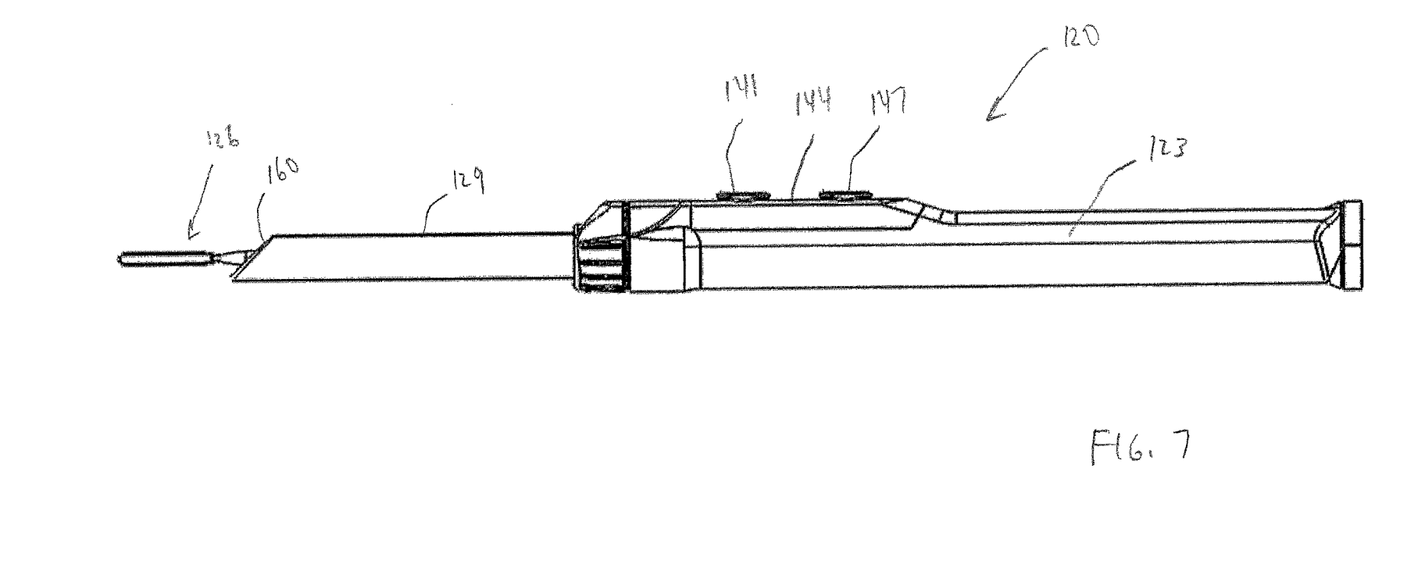
FIG. 7 is a side elevational view of the device of FIG. 5.

In FIG. 7, the orientation of the blade holder 133 in the center of the tube 129 is best shown based on the position of the electrode 126. The electrode 126 slides into the blade holder 133 and is held in place by a frictional fit inside the channel. As shown the end 160 of the tube 129 is shaped to have a cross section parallel to a user's line of sight toward the electrode 126 when using the pen 120. The vacuum tube 129 may be telescopically attached to the body 123 as will be evident to those of ordinary skill in the art based on this disclosure. The vacuum tube 129 may also be fixedly attached to the body 123. Electrodes 126 having different lengths, widths, etc. may be switched in and out of the blade holder 133 in the device to accommodate different patients and different procedures.

Figure 8:
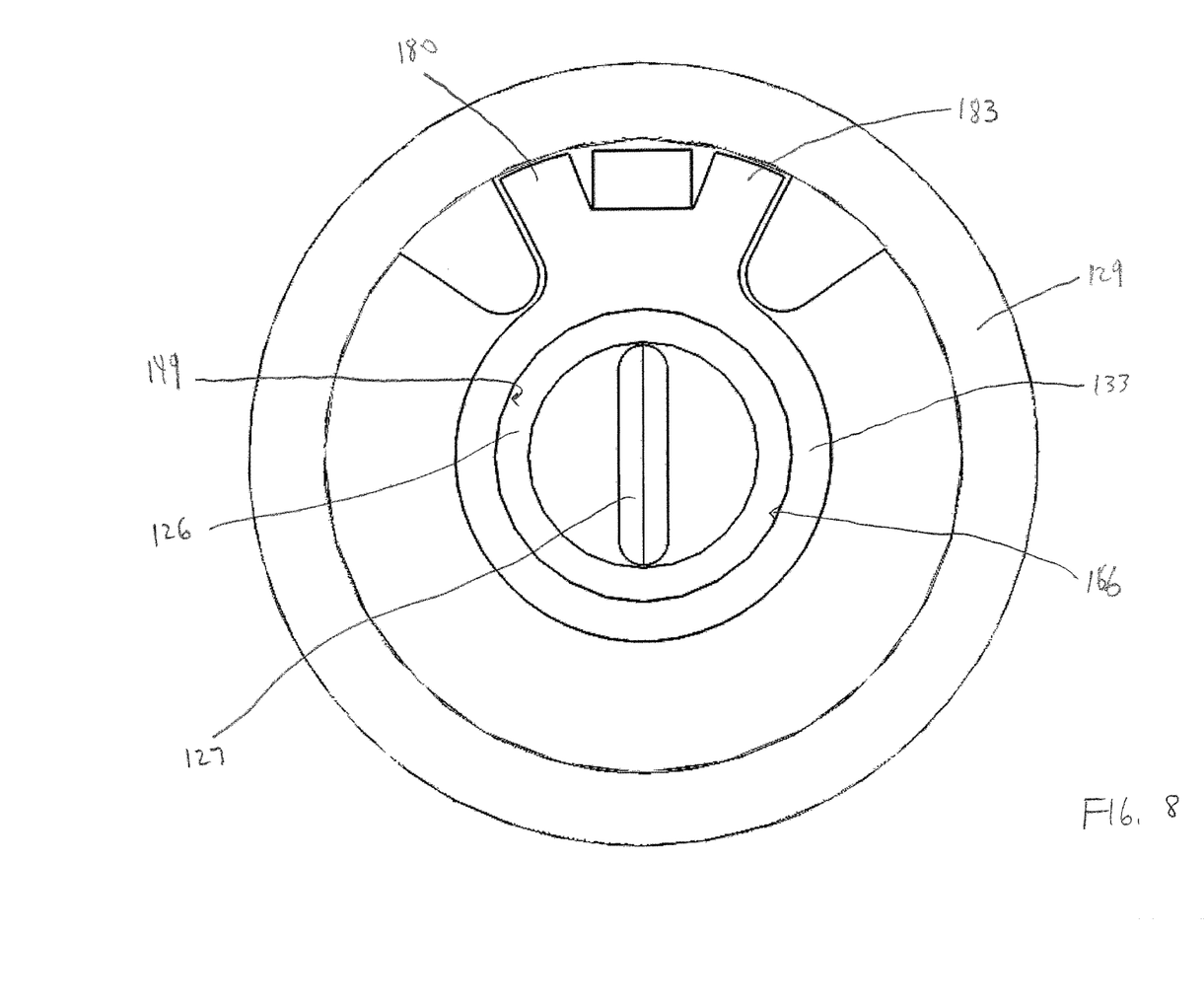
FIG. 8 is a front elevational view of the tube and electrode of the device of FIG. 5.

Turning to FIG. 8, a separate channel 149 is formed in the blade holder 133 for receiving the electrode 126. The surgical smoke is evacuated through the passageway formed around the blade holder 133 and its ribs 180, 183. The opening formed in the blade holder 133 mounted in the tube 129 is sized to interchangeably receive one or more electrodes 126. The opening leads to a channel 166 extending axially along the length of the tube 129. At the end of the channel 166, the base 130 of the electrode 126 contacts a conductor 156 to establish electrical contact between the electrode 126 and the electrical circuit (not shown) in the device 120. The electrical circuit in the device provides current to the electrode 126. The current may be provided at different levels depending on the application. For cutting, a higher current level is required, whereas, coagulation requires less current.

Figure 9:
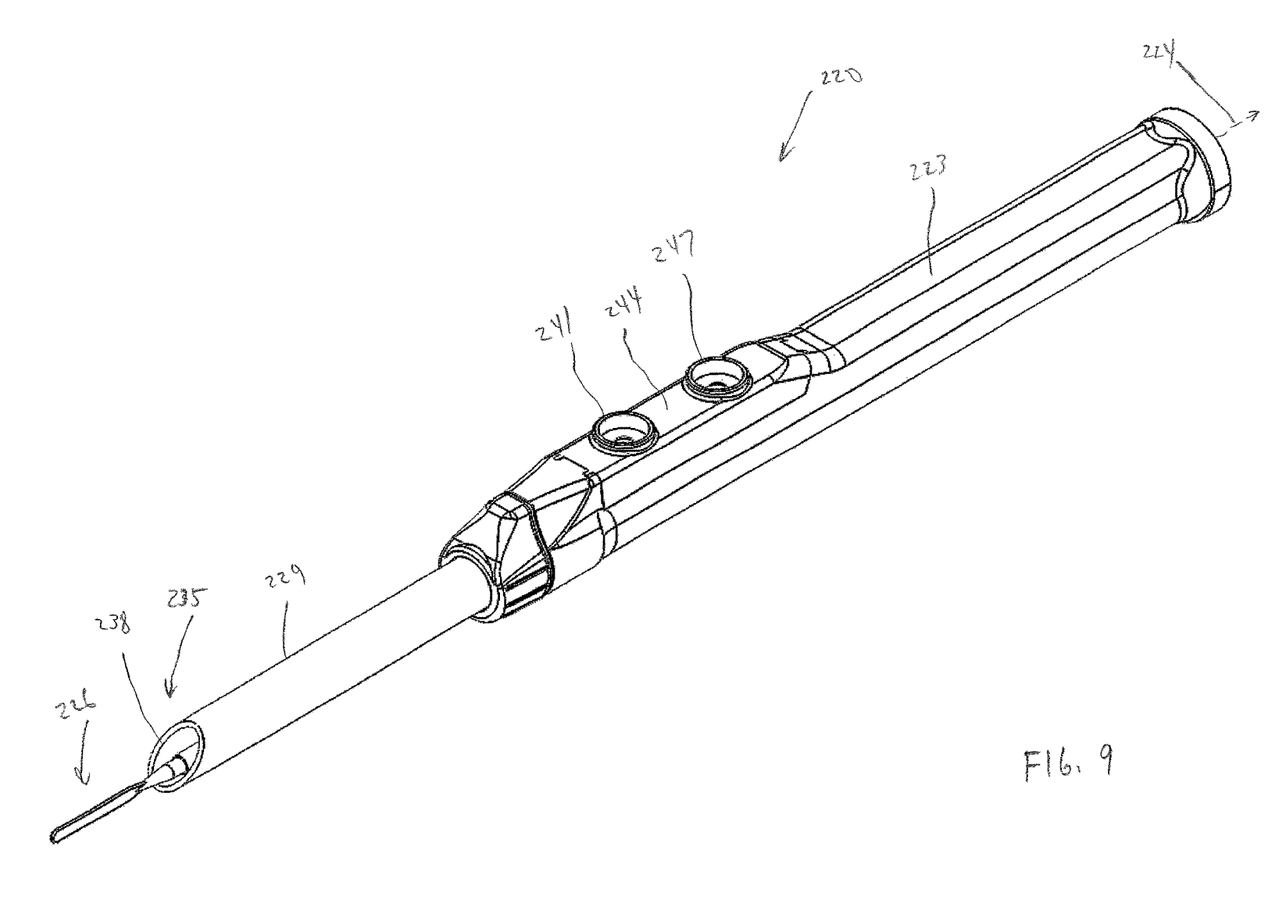
FIG. 9 is a perspective view of another alternate embodiment of the electrosurgical device of the present invention.

In FIG. 9, an alternate embodiment of the electrosurgical device is shown. A blade holder 233 (FIG. 10) is disposed inside the tube 229 but the electrode 226 is positioned at a bottom portion of the tube 229. The body 223 may be ergonomically shaped to be received by a user's hand. The body 223 may be pencil shaped and may have a longitudinal axis 224. On the left side of the figure, an electrode 226 is removably attached to a vacuum tube 229. The electrode 226 may have a uninsulated end portion 227, insulated portion 228, and a mounting portion 230. The vacuum tube 229 is mounted on the body 223 and extends from the body in an axial direction 232. The distal end 235 of the vacuum tube 229 comprises an inlet 238 shaped to have a cross section parallel to a user's line of sight toward the electrode 226 when using the pen 220.

The pen 220 may be provided with a first button 241 arranged on the external surface 244 of the body 223. The first button 241 may control the current flow to the device at a first level. The pen 220 may have a second button 247 for controlling a current flow at a second level to the electrode 226. Additional buttons may be added for controlling the vacuum source, a light source or the like.

Figure 10:
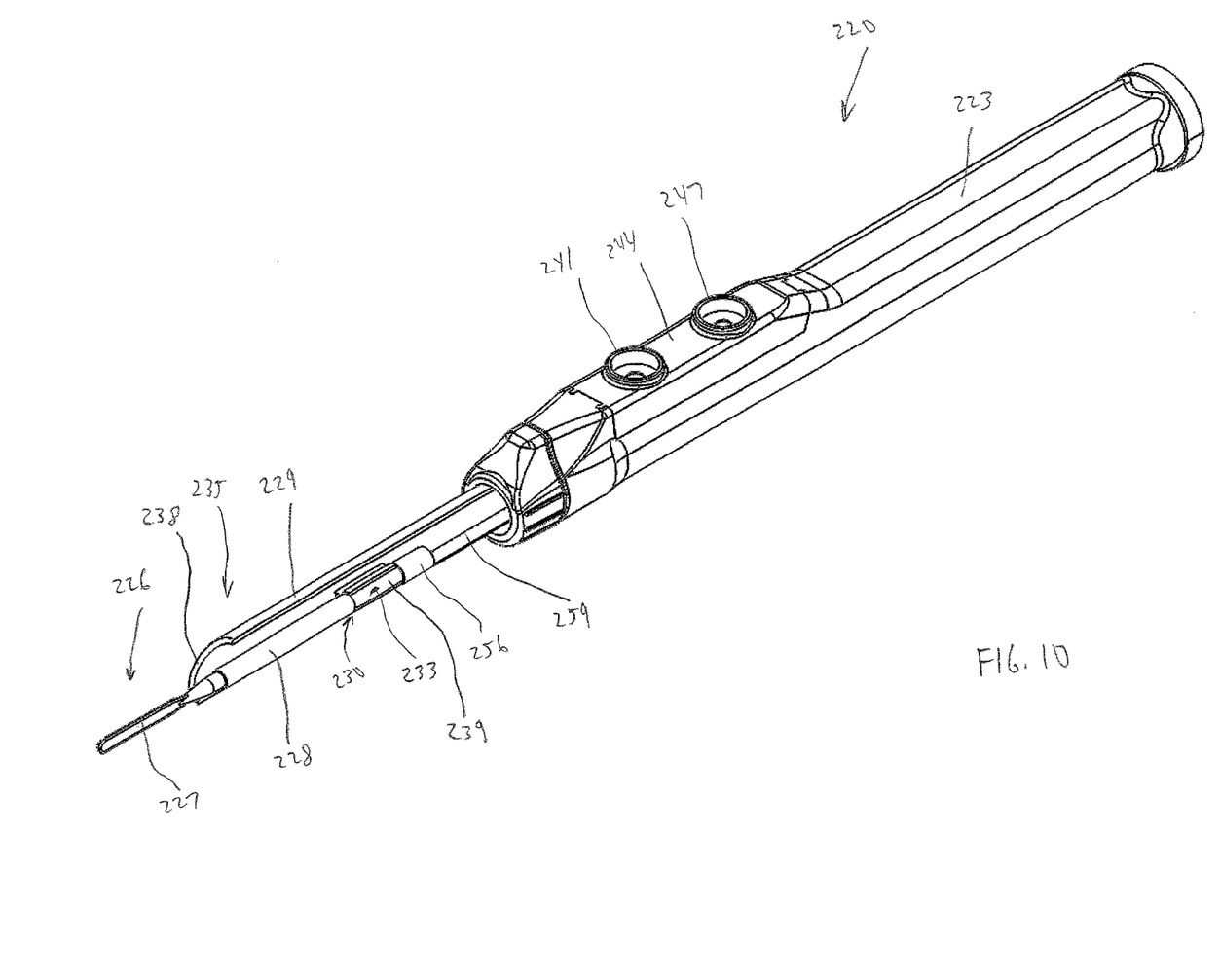
FIG. 10 is a partial cutaway perspective view of the electrosurgical device of FIG. 9.

Turning to FIG. 10, a portion of the vacuum tube 229 has been removed for clarity. The tube 229 has a channel/blade holder 233 defined therein for receiving the electrode 226. At the end of the channel, there is a conductor 256 that is electrically connected by an electrical connector 259 to a circuit inside the body 223 that provides current to the electrode 226 for operation of the device 220. The first and second buttons 241, 247 are electrically associated with the electric circuit inside the body 223 to provide different levels of current to flow to the electrode 226 depending on whether the device 220 is being used for cutting or coagulating. The end 227 of the electrode 226 is uninsulated for use as an electric blade for cutting and cauterizing during medical procedures. A midportion 228 of the electrode 226 is insulated so that the user can remove the electrode 226 from the device 220. A base portion 230 of the electrode 226 is designed to make contact with the conductor 256 at the end of the channel 233 in the tube 229 and to removably attach to the device 220 inside the tube 229. The blade holder 233 is mounted inside and toward the bottom of the vacuum tube 229. The blade holder 233 has a longitudinal opening for receiving the electrode 226. The body 239 of the blade holder 233 is round and fits inside the vacuum tube 229 toward the bottom of the tube 229. The blade holder 233 is attached to the inside of the tube 229. The blade holder 233 provides for the flow of surgical smoke around the blade holder 233 through the tube 229.

Figure 11:
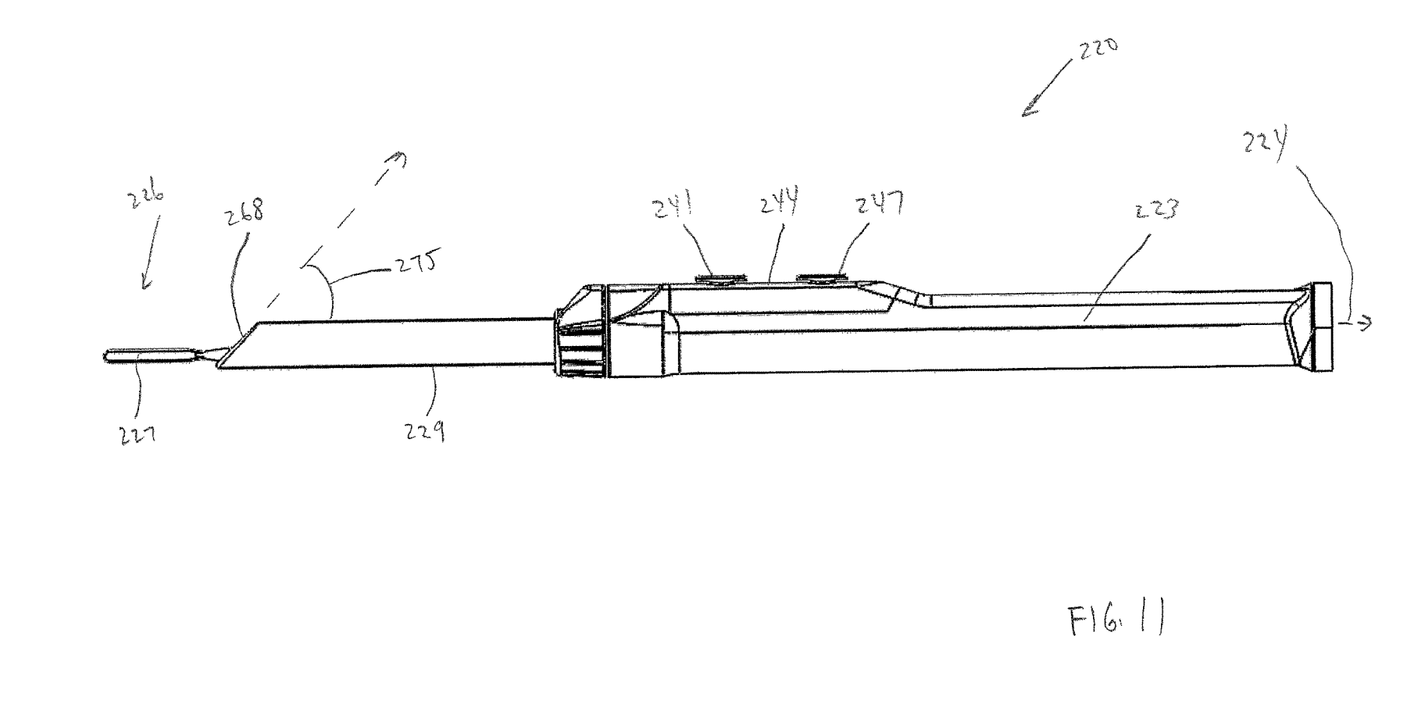
FIG. 11 is a side elevational view of the device of FIG. 9.

In FIG. 11, the placement of the blade holder 233 toward the bottom of the tube 229 is best shown based on the position of the electrode 226 relative to the tube 229. The electrode 226 slides into the blade holder 233 and is held in place by a frictional fit inside the channel. As shown the end of the tube 229 is shaped to have a cross section parallel to a user's line of sight toward the electrode 226 when using the pen 220. The end 268 of tube 229 is cut at an acute angle 275 relative to the longitudinal axis 224 of device 220. The vacuum tube 229 may be telescopically attached to the body 223 of the device 220 in the position shown or may be fixedly attached as will be evident to those of ordinary skill in the art based on this disclosure. Electrodes 226 having different lengths, widths, etc. may be switched in and out of the blade holder in the device to accommodate different patients and different procedures.

Figure 12:
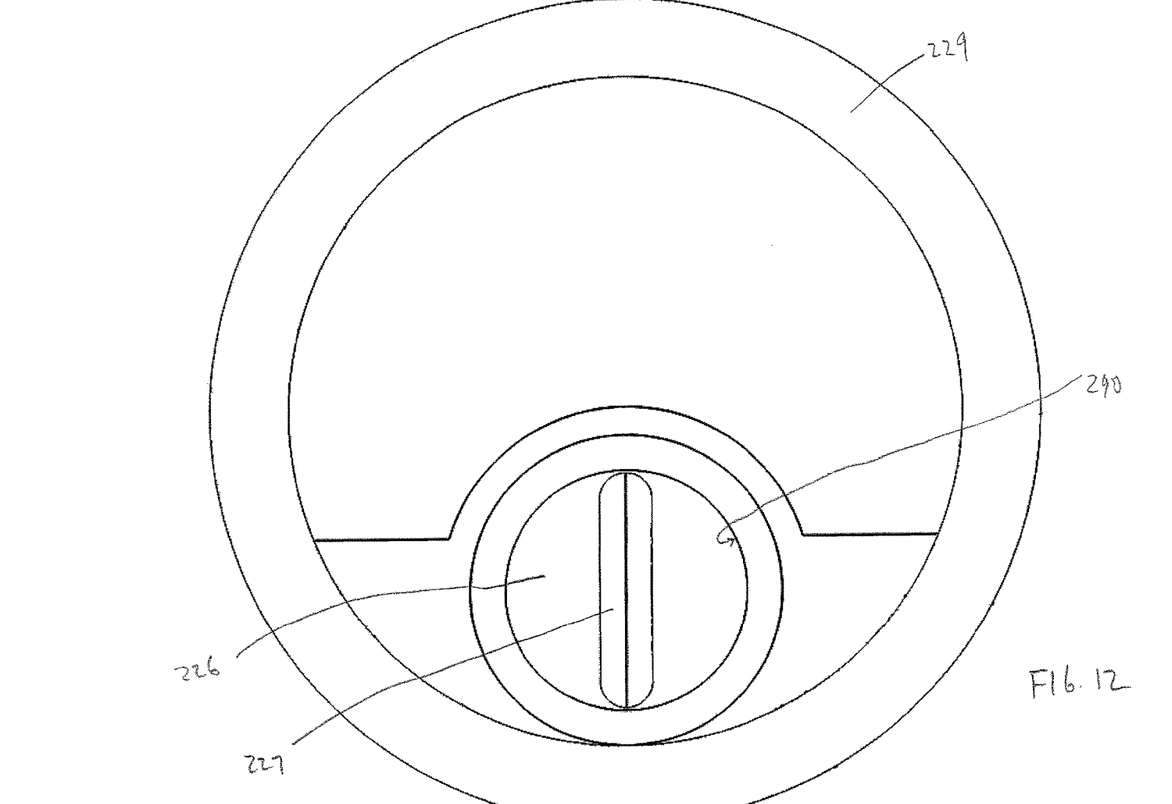
FIG. 12 is a front elevational view of the tube and electrode of the device of FIG. 9.

Turning to FIG. 12, a channel is formed in the blade holder 233 for receiving the electrode 226. The surgical smoke is evacuated through the passageway formed around the blade holder 233. An opening 290 formed in the blade holder 233 mounted in the tube 229 is sized to receive one or more electrodes 226. The opening 290 leads to a channel extending axially along the length of the tube 229. At the end of the channel 233 the base 230 of the electrode 226 contacts the conductor 256 to establish electrical contact between the electrode 226 and the electrical circuit in the device 220. The electrical circuit in the device 220 provides current to the electrode 226. The current may be provided at different levels depending on the application. For cutting, a higher current level is required, whereas, coagulation requires less current.

The present invention contemplates that many changes and modifications may be made. Therefore, while the presently-preferred form of the emissions measuring system has been shown and described, and several modifications and alternatives discussed, persons skilled in this art will readily appreciate that various additional changes and modifications may be made without departing from the spirit of the invention, as defined and differentiated by the following claims.

The invention claimed is:

1. An electrosurgical device comprising:
   an electrode having a first portion whose exterior is electrically uninsulated, a second portion whose exterior is electrically insulated, and a third portion;
   an elongated hollow body having an internal cavity, a front end, a rear end, an external surface, and an electrical circuit arranged within said body;
   a first button for controlling a current flow at a first level to said electrode and arranged on said external surface; and,
   a vacuum tube slidably engaged by said body and having an inlet generally facing said front end, said electrode mounted on said vacuum tube, said vacuum tube comprising (i) a passageway fluidly connected to said inlet operable for smoke evacuation formed at a top of said vacuum tube and (ii) a channel defined by a curved common wall with said passageway and an exterior wall of said vacuum tube, said channel disposed at a bottom of said vacuum tube adjacent a radial interior surface of said vacuum tube, said channel configured to reversibly receive said third portion of said electrode such that electrical contact is made between said electrode and said electrical circuit, wherein the vacuum tube comprises an inlet shaped to have a cross section parallel to a user's line of sight towards said electrode when using said device.

2. An electrosurgical device as set forth in claim 1 wherein said body is ergonometrically shaped to be received by a user's hand.

3. An electrosurgical device as set forth in claim 1 wherein said body is pencil shaped.

4. An electrosurgical device as set forth in claim 1 wherein said body contains friction striations.

5. An electrosurgical device as set forth in claim 1 wherein said electrode is monopolar, bipolar, or sesquipolar.

6. An electrosurgical device as set forth in claim 1 and further comprising a second button for controlling a current flow at a second level to said electrode.

7. An electrosurgical device as set forth in claim 1 and further comprising:
   a light source arranged to illuminate an area near said electrode;
   a battery for providing power to said light source; and
   a button for controlling said light source.

8. An electrosurgical device as set forth in claim 1 and further comprising a filter arranged within said internal cavity.

9. An electrosurgical device as set forth in claim 8 wherein said filter comprises an RFID tag containing filter information.

10. An electrosurgical device as set forth in claim 1 wherein said inlet has a substantially rectangular cross section.

11. An electrosurgical device comprising:
    an electrode;
    an elongated hollow body having an internal cavity, a front end, a rear end, an external surface, and an electrical circuit arranged within said body;
    said hollow body shaped to have an ergonometric orientation complementary to a user's hand;
    a first button for controlling a current flow at a first level to said electrode and arranged on said external surface; and,
    a vacuum tube slidably engaged by said body and having an inlet, said vacuum tube comprising (i) a passageway fluidly connected to said inlet at a top of said vacuum tube and (ii) a channel defined by a curved common wall with said passageway and an exterior wall of said vacuum tube, said channel disposed at a bottom of said vacuum tube adjacent an interior surface of said vacuum tube, said electrode mounted in said channel on said vacuum tube, the vacuum tube having a blade holder in said channel configured to reversibly receive said electrode in a central portion of the vacuum tube, wherein the vacuum tube comprises an inlet shaped to have a cross section parallel to a user's line of sight towards said electrode when using said device.

12. An electrosurgical device as set forth in claim 11 wherein said device is configured to have an electrically insulated portion not surrounded by said body when said electrode is received by said body.

13. An electrosurgical device as set forth in claim 11 wherein said body is pencil shaped.

14. An electrosurgical device as set forth in claim 11 wherein said body contains curved friction striations.

15. An electrosurgical device as set forth in claim 11 wherein said electrode is monopolar, bipolar, or sesquipolar.

16. An electrosurgical device as set forth in claim 11 and further comprising a second button for controlling a current flow at a second level to said electrode.

\* \* \* \* \*